(12) United States Patent
Corpa de la Fuente

(10) Patent No.: US 10,194,966 B2
(45) Date of Patent: Feb. 5, 2019

(54) BONE CEMENT REMOVAL USING REAL-TIME ACOUSTIC FEEDBACK

(71) Applicant: Blue Belt Technologies, Inc., Pittsburgh, PA (US)

(72) Inventor: Cedric Corpa de la Fuente, Pittsburgh, PA (US)

(73) Assignee: Blue Belt Technologies, Inc., Pittsburgh, PA (US)

( * ) Notice: Subject to any disclaimer, the term of this patent is extended or adjusted under 35 U.S.C. 154(b) by 663 days.

(21) Appl. No.: 14/846,015

(22) Filed: Sep. 4, 2015

(65) Prior Publication Data
US 2016/0066972 A1    Mar. 10, 2016

Related U.S. Application Data

(60) Provisional application No. 62/045,912, filed on Sep. 4, 2014.

(51) Int. Cl.
*A61B 17/16*    (2006.01)
*A61B 17/88*    (2006.01)

(52) U.S. Cl.
CPC ........ *A61B 17/8847* (2013.01); *A61B 17/164* (2013.01); *A61B 17/1626* (2013.01); *A61B 17/8811* (2013.01)

(58) Field of Classification Search
CPC ............ A61B 17/8847; A61B 17/1626; A61B 17/164
USPC ..................................................... 606/79–82
See application file for complete search history.

(56) References Cited

U.S. PATENT DOCUMENTS

| | | | |
|---|---|---|---|
| 4,873,969 A * | 10/1989 | Huebsch | A61B 17/1604 606/80 |
| 5,047,035 A | 9/1991 | Mikhail et al. | |
| 5,382,251 A | 1/1995 | Hood et al. | |
| 5,408,409 A | 4/1995 | Glassman et al. | |
| 6,205,411 B1 | 3/2001 | DiGioia, III et al. | |
| 6,336,931 B1 * | 1/2002 | Hsu | A61B 17/1626 606/130 |
| 6,665,948 B1 * | 12/2003 | Kozin | A61B 17/1626 175/45 |

(Continued)

FOREIGN PATENT DOCUMENTS

WO    2016037066 A1    3/2016

OTHER PUBLICATIONS

Chao et al. "Simulation and Animation of Musculosketal Joint System" (Nov. 1, 1993) J. Biomechanical Engineering 115(4B): 562-568.

(Continued)

*Primary Examiner* — Matthew J Lawson
(74) *Attorney, Agent, or Firm* — Pepper Hamilton LLP

(57) ABSTRACT

Systems and methods for bone cement removal using real-time acoustic feedback, such as during a drilling process in a revision arthroplasty, are discussed. A system for bone cement removal may include a processor to perform operation comprising receiving digital frequency data from the microphone, comparing at least a portion of the digital frequency data to a plurality of frequency signatures, and determining, based at least in part on the comparing, whether the portion of the digital frequency data is representative of a cut bone frequency or a cut bone cement frequency.

13 Claims, 6 Drawing Sheets

(56) References Cited

U.S. PATENT DOCUMENTS

| | | | |
|---|---|---|---|
| 6,790,211 B1* | 9/2004 | McPherson | A61B 17/8847 606/169 |
| 8,463,421 B2 | 6/2013 | Brett et al. | |
| 9,936,961 B2* | 4/2018 | Chien | A61B 17/1626 |
| 2005/0116673 A1 | 6/2005 | Carl et al. | |
| 2005/0131415 A1* | 6/2005 | Hearn | A61B 17/1626 606/80 |
| 2006/0178593 A1* | 8/2006 | Neubardt | A61B 17/1626 600/547 |
| 2007/0196784 A1* | 8/2007 | Bochi | A61B 17/1626 433/114 |
| 2008/0262347 A1 | 10/2008 | Batchelder et al. | |
| 2009/0245956 A1* | 10/2009 | Apkarian | A61B 17/1626 408/1 R |
| 2011/0256496 A1* | 10/2011 | Arzanpour | A61C 1/0007 433/27 |
| 2012/0053492 A1* | 3/2012 | Chang | A61B 17/1624 601/2 |
| 2014/0120496 A1* | 5/2014 | Rothenwaender | A61C 1/05 433/132 |
| 2015/0066038 A1* | 3/2015 | McGinley | A61B 17/16 606/80 |
| 2015/0342618 A1* | 12/2015 | Nguyen | A61B 17/1626 433/27 |
| 2016/0089154 A1* | 3/2016 | Chien | A61B 17/1626 606/79 |
| 2016/0361070 A1* | 12/2016 | Ardel | A61B 17/1626 |
| 2017/0112579 A1* | 4/2017 | Yen | A61B 34/30 |
| 2017/0348010 A1* | 12/2017 | Chiang | A61B 90/03 |

OTHER PUBLICATIONS

Chinese Office Action for CN20130058810.6 dated Feb. 6, 2017.
Chinese Office Action for CN201480027135.5 dated Jan. 17, 2017.
Delp et al. "An Interactive Graphics-Based Model of the Lower Extremity to Study Orthopaedic Surgical Procedures" (Aug. 1990) IEE Transactions on Biomedical Engineering 37(8): 757-767.
DiGioia et al. "An Integrated Approach to Medical Robotics and Computer Assisted Surgery in Orthopaedics" (1995) Carnegie Mellon University 106-111.
DiGioia et al, "HipNav: Pre-operative Planning and Intra-operative Navigational Guidance for Acetabular Implant Placement in Total Hip Replacement Surgery" (Nov. 1995) Preceedings of CAOS '96 1-8.
Harris et al. "Experiences with Robotic Systems for Knee Surgery" (Mar. 19-22, 1997) Springer-Verlag, London, UK 757-766.
Freysinger et al, "A Passive-Marker-Based Optical System for Computer-Aided Surgery in Otorhinolaryngology: Development and First Clinical Experiences" (Feb. 2002) The Laryngoscope 112(2):409.
O'Toole III et al. "Towards More Capable and Less Invasive Robotic Surgery in Orthopaedics" (1995) Computer Vision, Virtual Reality and Robotics in Medicine 905: 123-130.
Taylor et al. "An Image-Directed Robotic System for Precise Orthopaedic Surgery" (Jun. 1994) IEE Transactions on Robotics and Automation 10 (3): 261-275.
Troccaz et al. "The Use of Localizers, Robots and Synergistic Devices in CAS" (Nov. 21, 2005) First Joint Conference: Computer Vision, Virtual Reality and Robotics in Medical and Medical Robotics and Computer-Assisted Surgery 1205: 725-736.
Dillman et al. "Haptic Devices in Medical Applications" (Jun. 23, 1999) Institute for Process Control and Robotics, 1st International Workshop, Paris, France, pp. 12-22.
International Search Report and Written Opinion for PCT/US2015/048558 dated Nov. 25, 2017.
Yu Sun, Haiyang Jin, Ying Hu, Peng Zhang, Jianwei Zhang, State Recognition of Bone Drilling With Audio Signal in Robotic Orthopedics Surgery System, 2014 IEEE/RSJ International Conference on Intelligent Robots and Systems (IROS 2014), Sep. 14-18, 2014, 6 pages.

* cited by examiner

BONE CEMENT REMOVAL USING REAL-TIME ACOUSTIC FEEDBACK

CLAIM OF PRIORITY

This patent application claims the benefit of priority of U.S. Provisional Patent Application Ser. No. 62/045,912, titled "Bone Cement Removal Using Real-Time Acoustic Feedback," filed on Sep. 4, 2014, which is hereby incorporated by reference herein in its entirety.

TECHNICAL FIELD

The present invention relates to systems and methods in the field of joint arthroplasty, more specifically, revisions of joint replacements.

BACKGROUND

Replacement of prosthetic joints often becomes necessary, even in the best of situations. Sometimes an infection develops or a prosthetic fails, but other times, the prosthetic is simply worn out. Regardless of the reason, replacement (or "revision" as it is sometimes called) poses a difficult problem for a surgeon in that more bone will need to be removed to enable the new prosthetic to fit tightly, but it is best to remove as little additional bone as possible.

In hip arthroplasty, for example, a prosthesis stem portion is placed in the intramedullary canal of the femur and stabilized with a cement mantle. When a revision joint arthroplasty surgery is performed, the stem from the previous prosthesis needs to be removed and consequently so does the cement mantle used for the implant. To remove the cement mantle a surgical drill or bur is used. All previous techniques that use drills and burs to remove the cement mantle, however, also run a high risk of removing additional bone unnecessarily.

To combat this problem, some previous technologies focused on guiding the drill so that it is aligned to not do any damage. U.S. Pat. No. 5,047,035 to Mikhail et al. discloses a system for performing hip prosthesis revision surgery that includes a trial femoral component having a passageway which, upon insertion into the cavity remaining after removal of the original prosthesis, provides guide means for drilling a channel to receive a guide wire which, upon removal of the trial femoral component, serves as guide means for progressively larger reamers. Alternatively, stopping a surgical drill once it breaks through a workpiece so that no unintended damage is done is disclosed in U.S. Pat. No. 8,463,421 to Brett et al. In Brett, a control breakthrough method is described wherein the speed of the drill bit is controlled by continually measuring the force and torque on the drill bit during the procedure and calculating the rate of change in the force and torque so that soft tissues are not damaged. Neither of these technologies, however, has been brought to bear on the problem of removing cement while maintaining bone during revision surgery.

SUMMARY

There is a need for a system to enable the removal of cement mantle from inside a bone, when using a surgical drill or bur, that minimizes the risk of removing an undesired portion of or additionally damaging the bone. In short, there is a need for a system that stops or withdraws the drill or bur when it breaks through the cement mantle and contacts the bone so that bone is not removed unnecessarily.

A system of the present invention controls the speed of a drill or a bur, or alternatively retracts the bur at the appropriate time, by using real-time acoustic feedback. In an example, during the drilling process in a revision arthroplasty, the surgeon drills inside a patient's bone to remove the old cement mantle and the system compares the acoustic frequency to a library of frequencies in a database. If, during the drilling process, the observed acoustic feedback differs from the frequency produced at the cement mantle/bur interface (i.e. the drill or bur contacts bone); the drill or bur may be automatically stopped or retracted away from the bone surface by the system. In an example, the bur is retracted into a protective sleeve to prevent bone damage.

In an example, the database may include pre-recorded frequencies produced by numerous alternative cement mantle/bur interface combinations. Alternatively, the resonance frequency of the specific cement mantle being drilled may be used to make this determination. In still another example, the drill or bur may be stopped or retracted when the frequency of the bone/bur interface or the resonance frequency of the bone is detected by acoustic feedback.

BRIEF DESCRIPTION OF THE DRAWINGS

Various example are illustrated by way of example in the figures of the accompanying drawings. Such example are demonstrative and not intended to be exhaustive or exclusive example of the present subject matter.

DETAILED DESCRIPTION

The removal of cement mantle in the femur during arthroplasty revision is a delicate operation because of the narrow workspace and reduced visibility of the workspace. Likewise, other revision surgeries suffer from the same problems. Giving surgeons the ability to stop, slow, or retract a drill or a bur once bone is contacted will reduce the risk of removing healthy bone unnecessarily. A system discussed below uses real time acoustic feedback to detect the sound of the bur or drill against cement material, such as bone cement, and to differentiate that sound from the sound of the drill or bur against bone or other materials. When this difference is detected, stopping, slowing, or retracting the drill or bur may be automatically performed.

Figure 1:
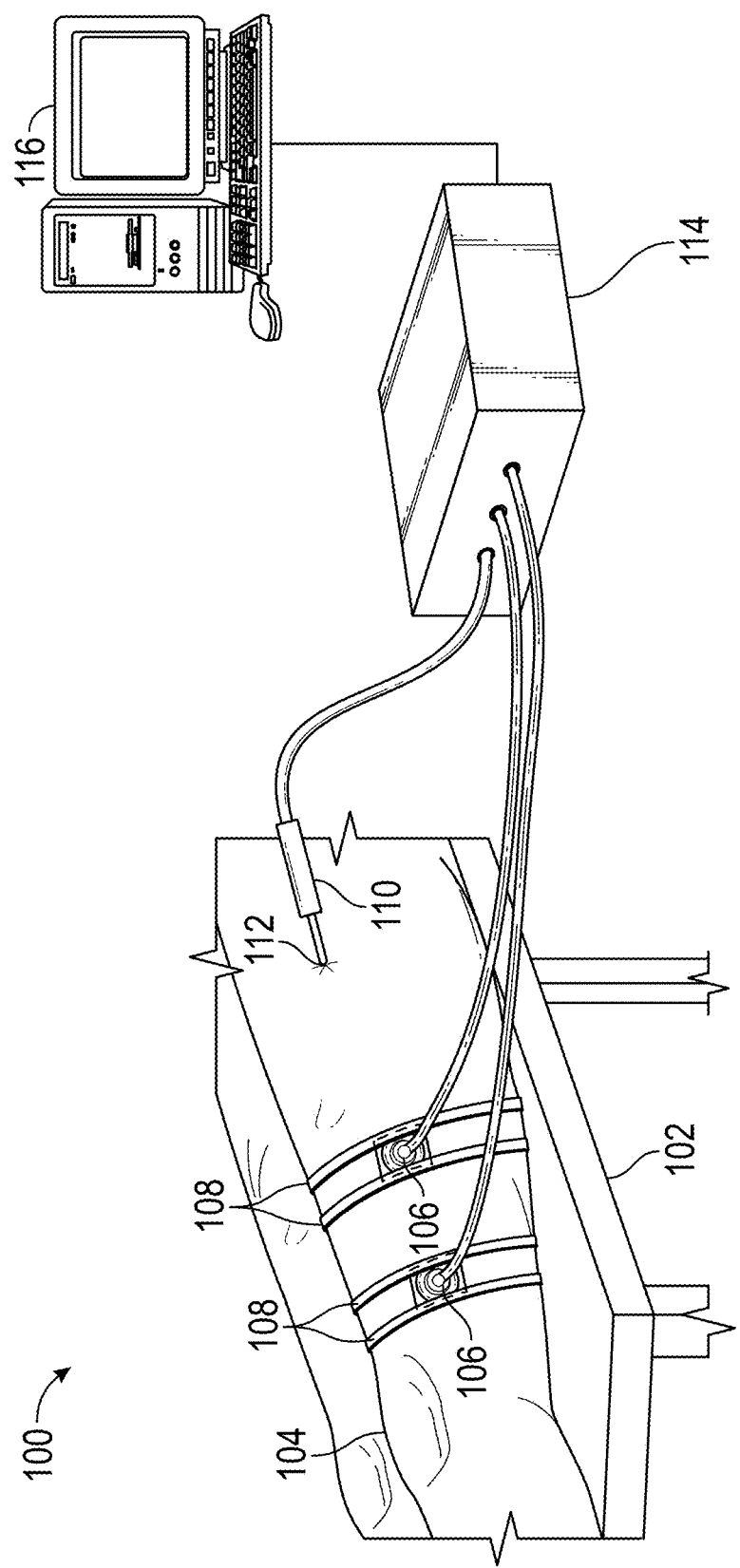
FIG. 1 illustrates an example of an acoustic feedback system.

FIG. 1 illustrates an example of an acoustic feedback system 100, such as may be used during a hip revision arthroplasty. The acoustic feedback system 100 may include microphones 106, straps 108 to secure the microphones 106 to a patient leg 104 on a surgical table 102. The acoustic feedback system 100 may include a handpiece 110 to control a cutting tool through a cut 112 in the patient leg 104 to access the bone cement for cutting it out. The handpiece 110 may connect to a control unit 114, which may connect to a computer 116, including a monitor.

In an example, the microphones 106 may include directional microphones. The microphones 106 may be placed directly on the patient's skin (e.g., on patient leg 104), such as by adhesively attaching or strapping them on. The microphones 106 may be oriented toward the workspace (e.g., facing the medullary canal) along a cutting axis to capture the sound of the spinning drill or bur as it comes into contact with surfaces, such as the residual cement inside the intramedullary canal or the patient's bone. In another example, a single microphone can be used to simplify the set-up. In yet another example, a plurality of microphones may be used to increase consistency and allow for better data matching. In yet another example, the microphones 106 may be placed on a drill (not shown), such as on handpiece 110.

In an example, the microphones 106 may work similar to an electronic stethoscope. The acoustic feedback system 100 may utilize any software package that works with microphones to record sound frequencies. The software may also be capable of measuring different channels, which may include a stethoscope-like channel. The microphone instrumentation may be easily configurable, easily removable from a patient, and may have a small footprint in the operating room and on the patient. The acoustic feedback system 100 may be utilized with drills or burs from virtually any manufacturer interchangeably. However, in some examples, different drills or burs may produce different acoustic signatures that would need to be accounted for with the database or matching algorithms. For example, configuration of the system can include entering the model number of the cutting tool and bur, which causes the system to operate from a specific portion of the database or adjust matching a matching algorithm accordingly.

The microphones 106 may be connected, in any manner known in the art, to the control unit 114, which may also be referred to as an electronics interface. The control unit may condition and filter signals picked up by the microphones 106, and may transform them to the frequency domain via a high performance real-time digital signal processor. High-speed communications may connect the control unit to a computer 116 of the kind known in the art. The computer 116 has access to a database of frequency signatures that may correspond with the current data acquired from the control unit 114. The output of comparing the frequency signatures to the acquired data may result in a level of confidence of recognition of cement drilling.

Figure 2:
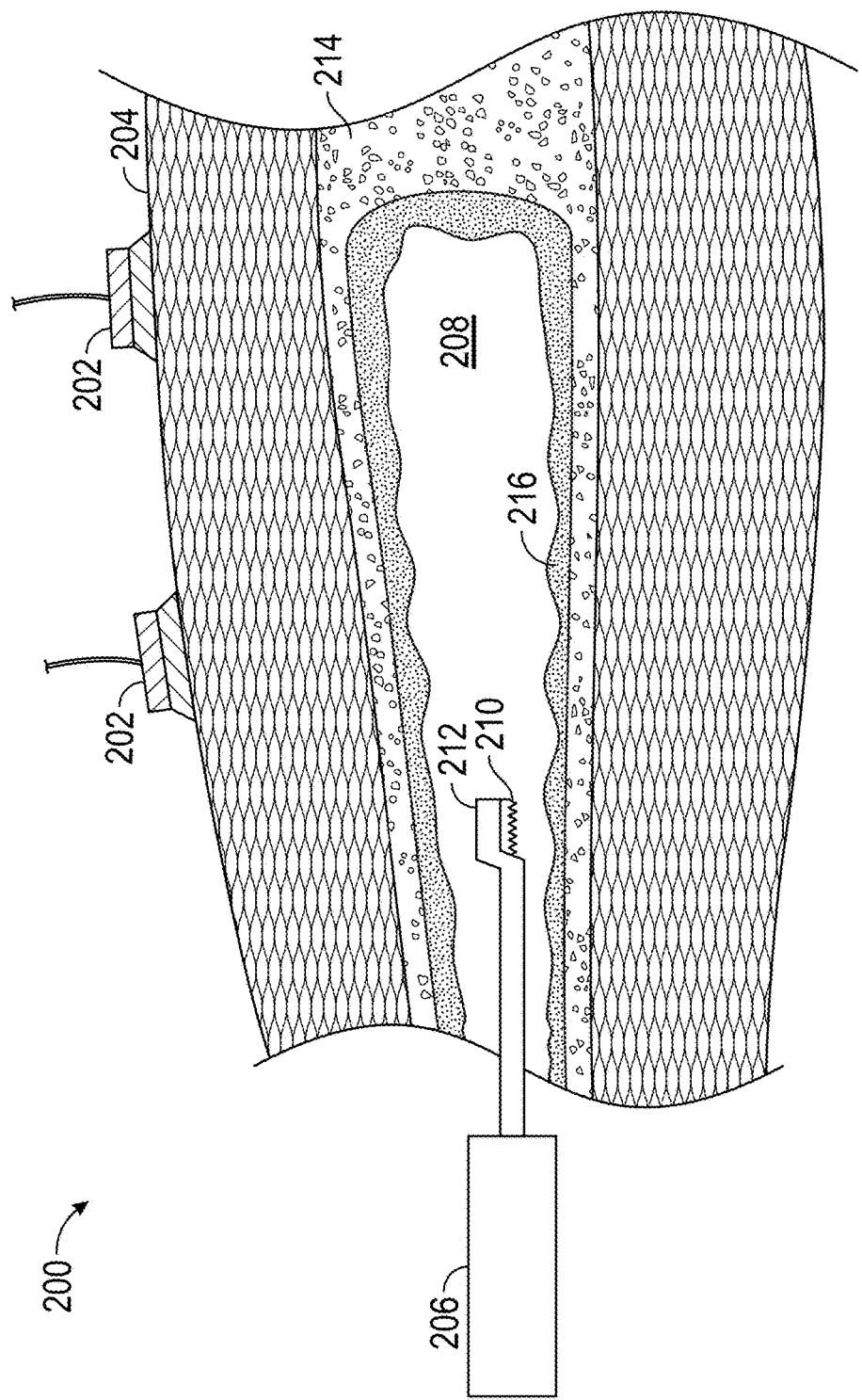
FIG. 2 is an illustration of an example bone cement removal system using acoustic feedback.

FIG. 2 is an illustration of an example bone cement removal system 200 using acoustic feedback. The bone cement removal system 200 may include a microphone or microphones 202 connected to patient skin 204, and a cutting tool, including a handpiece 206, a guard 212, and a bur 210. The cutting tool may be used to remove bone cement 216 in a hip cavity 208 of a femur bone 214.

When the bur 210 removes all of the bone cement 216 between the bur and the bone 214, the bur 210 will contact the bone 214, which causes the bone 214 to be stripped away. To minimize the bone 214 that is lost, the microphones 202 detect frequency changes from the bur 210 on bone cement 216 frequencies to the bur 210 on bone 214 frequencies. Once these changes are detected, the cutting tool receives an indication from a controller to slow, stop, or retract the bur 210. For example, when the bur 210 contacts the bone 214, the microphones 202 send detected audio signals to a digital signal processor, which then converts the detected audio signals to the frequency domain and sends resulting frequencies to a computer. The computer compares the resulting frequencies to frequency signatures stored in a database and determines whether the resulting frequencies are from the bur 210 contacting bone cement 216 or bone 214. When the resulting frequencies are from the bur 210 contacting bone 214, the computer finds a matching known bur-on-bone frequency in the frequency signatures, and instructs the controller to slow, stop, or retract the bur 210. The bur 210 is then slowed, stopped, or retracted away from the bone 214. At this point, the surgeon may adjust the handpiece 206 to move the bur 210 and continue to scrape the bone cement 216 in a different place, knowing that the bone cement was removed at that particular place and that only bone remains there.

Figure 3:
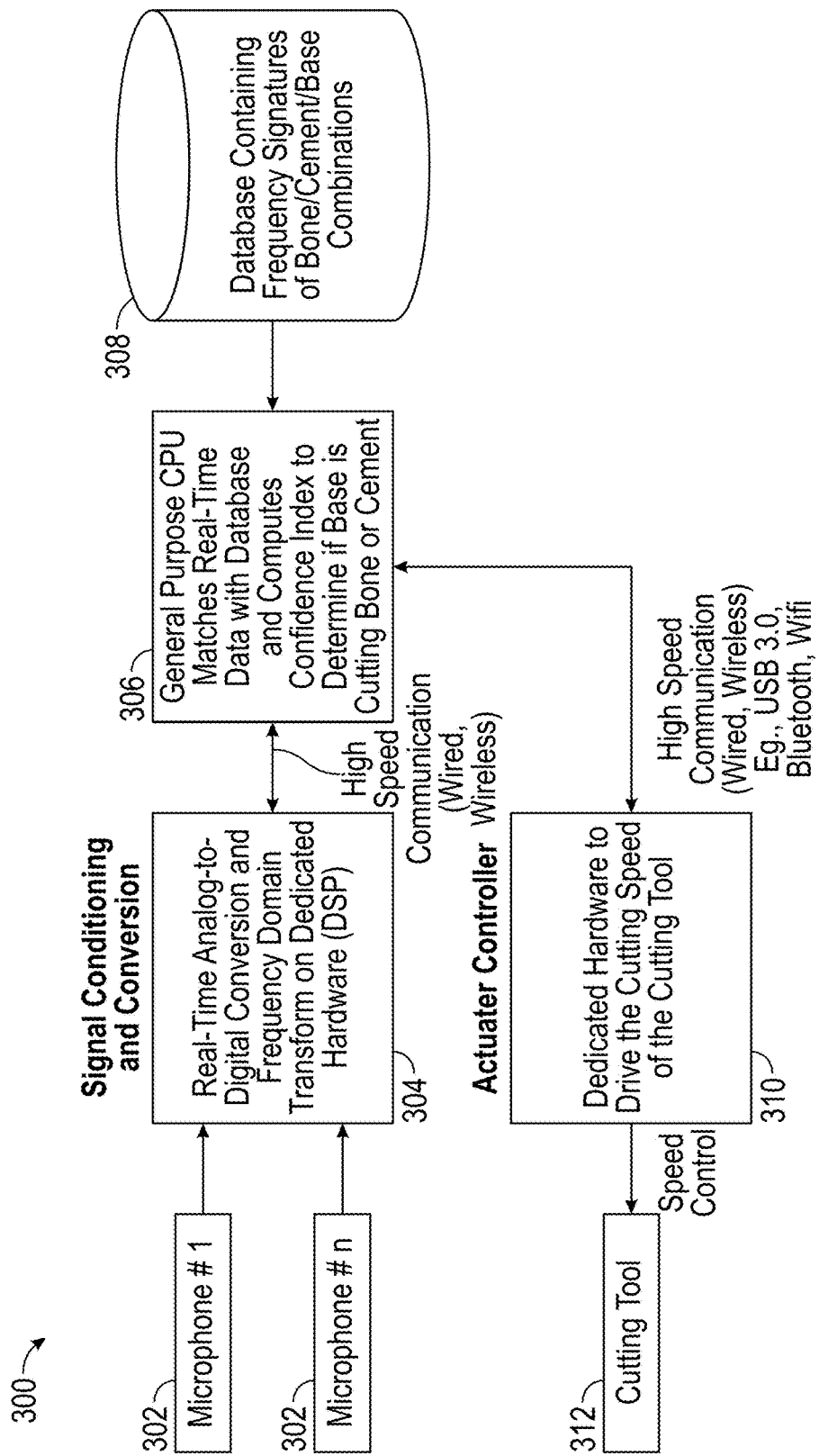
FIG. 3 is a block diagram that illustrates an example of an acoustic signal receiver and bone cement removal control system.

FIG. 3 is a block diagram that illustrates an example of an acoustic signal receiver and bone cement removal control system 300. The system 300 may include a microphone or microphones 302, a signal conditioning and conversion block 304, such as digital signal processor (DSP). The DSP may include hardware or software for a real-time analog-to-digital converter (ADC) and a frequency domain transform. Block 304 may be connected with a computer 306 via a high speed communication link (e.g., wireless, such as over Bluetooth or Wi-Fi, or wired, such as using USB 2.0 or 3.0, LAN, etc.). The computer 306 may include a Graphic Processor Unit (GPU), which may beneficially take advantage of the highly parallel architecture of a GPU. In this example, the computer 306 is used to compare real-time data received from block 304 with a database 308 of frequency signatures. The database 308 includes the frequency signatures, which may include bone frequencies, bone cement frequencies, soft tissue frequencies, air frequencies, combinations of frequencies, or the like. The frequency signatures may include frequencies for different burs, bones (e.g., bone densities, bone lengths, etc.), cement types, cement age, cement volume, or different combinations of these factors. The computer 306 may determine a confidence index when comparing the real-time data with the frequency signatures. The confidence index may include a confidence interval, a level of likelihood that the match is correct, a best-fit interval, a significance level, p-level, or other statistical qualifier for the results of the comparison. The computer 306 determines if the bur is in contact and cutting bone, bone cement, or other tissue/material, depending upon the acoustic signatures being compared.

The computer 306 may connect with a controller 310 via a high speed communication method (e.g., those described above for the connection between block 304 and the computer 306). The controller 310 may include dedicated hardware, or a combination of hardware and software, to drive a cutting speed of a cutting tool, control a depth of the cutting tool, or other similar control parameters associated with a particular cutting instrument. The controller 310 may include an actuator controller. The controller 310 connects to a handpiece or cutting rod 312 of a cutting tool, and may control speed of a bur at the end of the cutting tool. In an example, comparing the real-time data from block 304 to the frequency signatures from the database 308 is optimized by parallel computing, such as by using a Graphic Processor Unit (GPU). As such, even a general purpose GPU, such an example of computer 306, is incorporated into the system 300 to form a specialized computing and control system in combination with signal conditioning and conversion 304, database 308, and controller 310.

In an example, the controller 310 is commanded by the computer 306 via the appropriate data connection. The computer 306 output commands the drill based on specified parameters via the controller 310. For example, the drill may be enabled when the interface of bur and cement drilling acoustic frequency is detected, but stopped, slowed down, or retracted when a different acoustic frequency, such as the one associated with bur on bone, is detected. In another example, the resonance frequency of the bone cement may be detected and signal that the drilling should be maintained (e.g., continue to drive the cutting tool at the cutting speed). In yet another example, the detection of the resonance frequency of bone or acoustic frequency of bone on bur may produce a signal that results in a stop, slowdown, retraction of the cutting element or an alert. In these examples, an acoustic signature that indicates that the cutting element is not engaging any material is processed, and inputs from the surgeon (e.g., user) are maintained without modification.

In an example, a library of frequencies (e.g., frequency signatures) associated with bur to bone cement contact and bur to bone contact may be generated and stored in the database 308. The library may contain a collection of frequency signatures from several acoustic records of "bur on bone" and "bur on cement" interfaces. For the "bur on bone" interface, acoustics from various bone densities against a given bur at a given drilling speed may be collected and catalogued. For the "bur on cement" interface, acoustics from a given brand of bone cement against a given bur at a given speed may be collected and included in the library. In another example, fundamental or harmonic frequencies of specific formulations of bone cement or the fundamental or harmonic frequencies of different bone densities may be included in the database 308 as frequency signatures.

In an example, the system may work similarly to speech recognition and may use speech-to-text type algorithms. A large collection of frequency signatures may be filtered out until the most likely candidate is selected using fuzzy logic or a dynamic programming algorithm, such as a Viterbi algorithm, for example. In another example, the output of the algorithm that is selected may include two categories: cutting bone or cutting cement (or in some examples three categories: no cutting, cutting bone or cutting cement). The frequency signatures may be patient independent. The database 308 may be large enough to represent various density of bones in combination with supported burs and cements. In the case of patient dependent signatures, training of example acoustic signatures may be required at the on set of a cement removal procedure.

In an example, the cross correlation or comparison from data sent by block 304 and the database 308 can be done by the computer 306 in real-time. In an example, comparing the data from block 304 to the database 308 (e.g., frequencies output by a microphone to frequency signatures) may include an audio or acoustic fingerprinting algorithm. An acoustic fingerprinting algorithm may include a digital summary of audio data that compares characteristics of the received data to the frequency signatures. The acoustic fingerprinting algorithm may be done by a GPU of the computer 306.

Figure 4:
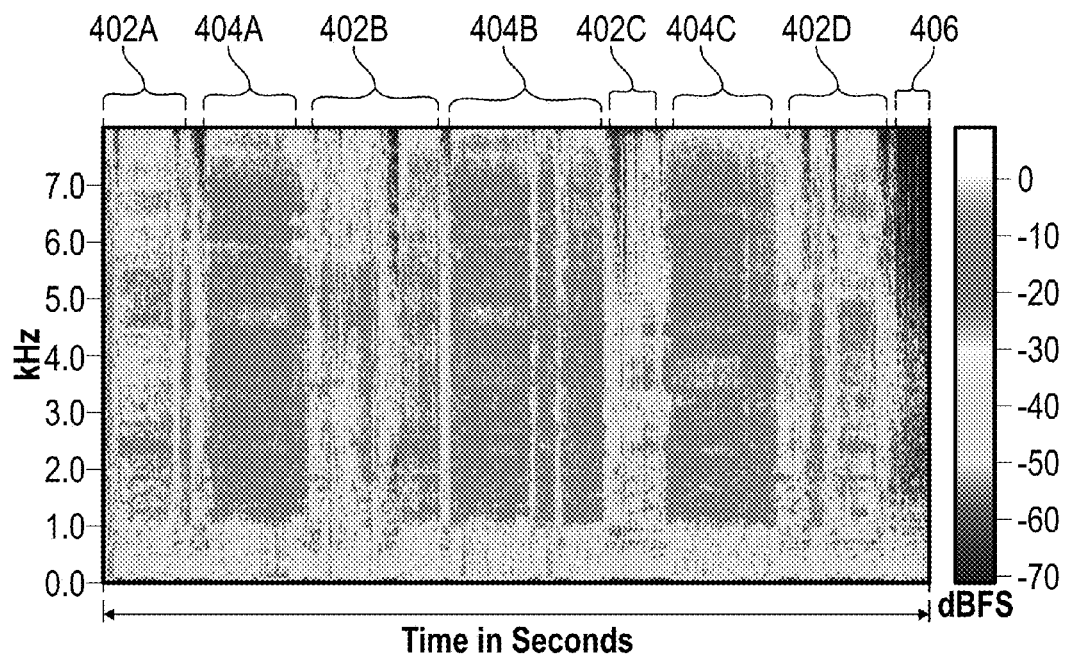
FIG. 4 is an illustration of an example spectrogram output of a bone cement removal session with high density bone.
Figure 5:
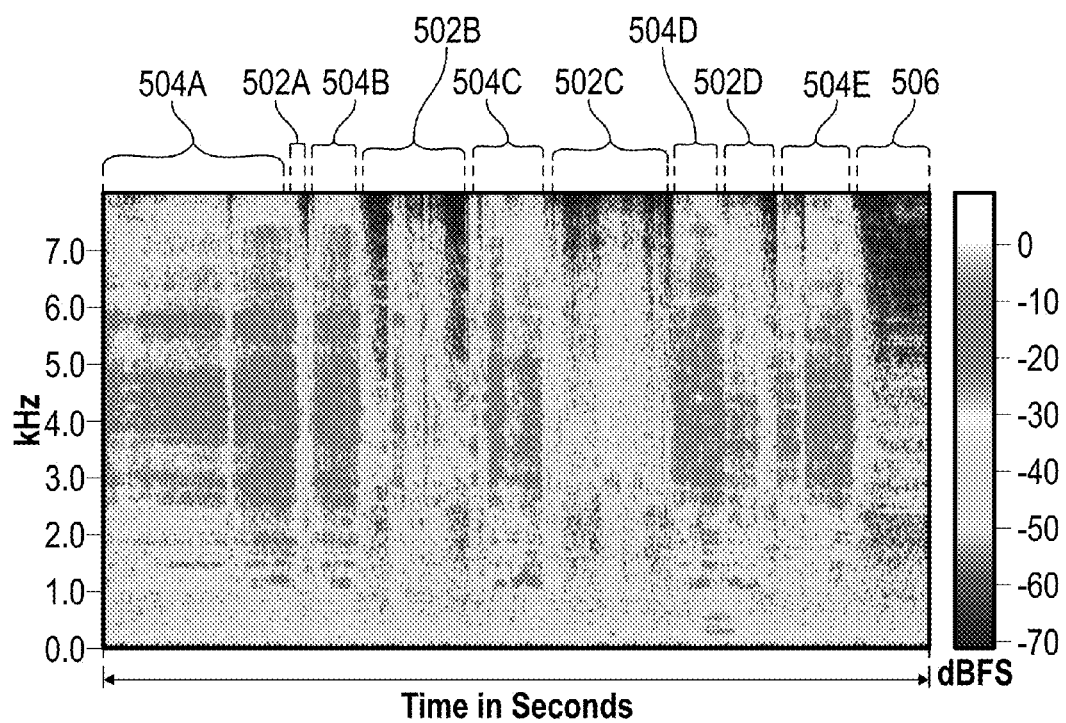
FIG. 5 is an illustration of an example spectrogram output of a bone cement removal session with low density bone.

FIG. 4 is an illustration of an example of a spectrogram output of a bone cement removal session with high density bone and FIG. 5 is an illustration of an example of a spectrogram output of a bone cement removal session with low density bone. The sound made by contact between materials and the bur may be described by using a spectrogram where outstanding frequencies may be observed and recognized as pattern. These patterns may be differentiated depending on the type of surface being cut.

FIGS. 4 and 5 show frequency outputs where contact was made between a bur and bone cement (e.g. 404A-C or 504A-E) and where contact was made between the bur and bone (e.g., 402A-D or 502A-D), as well as where neither bone or bone cement were cut (e.g., 406 or 506). The spectrogram outputs in FIGS. 4 and 5 include a fifteen second interval along the x-axis and a measurement of frequency (decibels on the left and kilohertz on the right) along the y-axis. FIG. 4 includes time periods where contact was made between bur and bone (e.g., 402A-D), which differ from similar time periods in FIG. 5 (e.g., 502A-D) in that the density of the bone cut in FIG. 4 is higher than the density of the bone cut in FIG. 5. The change in density of the bone causes different frequencies to be captured and displayed for those time periods in FIGS. 4 and 5. The different frequencies would then match (when compared by a computer) to different frequency signatures. Despite the different frequencies in those time periods in FIGS. 4 and 5, a system comparing these frequencies to frequency signatures in a database would be able to detect that bone was cut and instruct the bur to slow, stop, or withdraw.

Cutting bone emits a different frequency signature (including, e.g., different fundamental and harmonic frequencies) than bone cement. Since bone and bone cement are composed of different material, fundamental and harmonic frequencies in bone differ from those of bone cement. As described above, sound captured by a microphone is processed in real-time in the frequency domain and then compared to a plurality of frequency signatures in a database. The real-time processing enables differentiation between the frequency signature emanated from the cutting interface of bone/bur and bone cement/bur, signaling the feedback sensor whether to automatically control/stop the speed or extension of the drill or bur.

Figure 6:
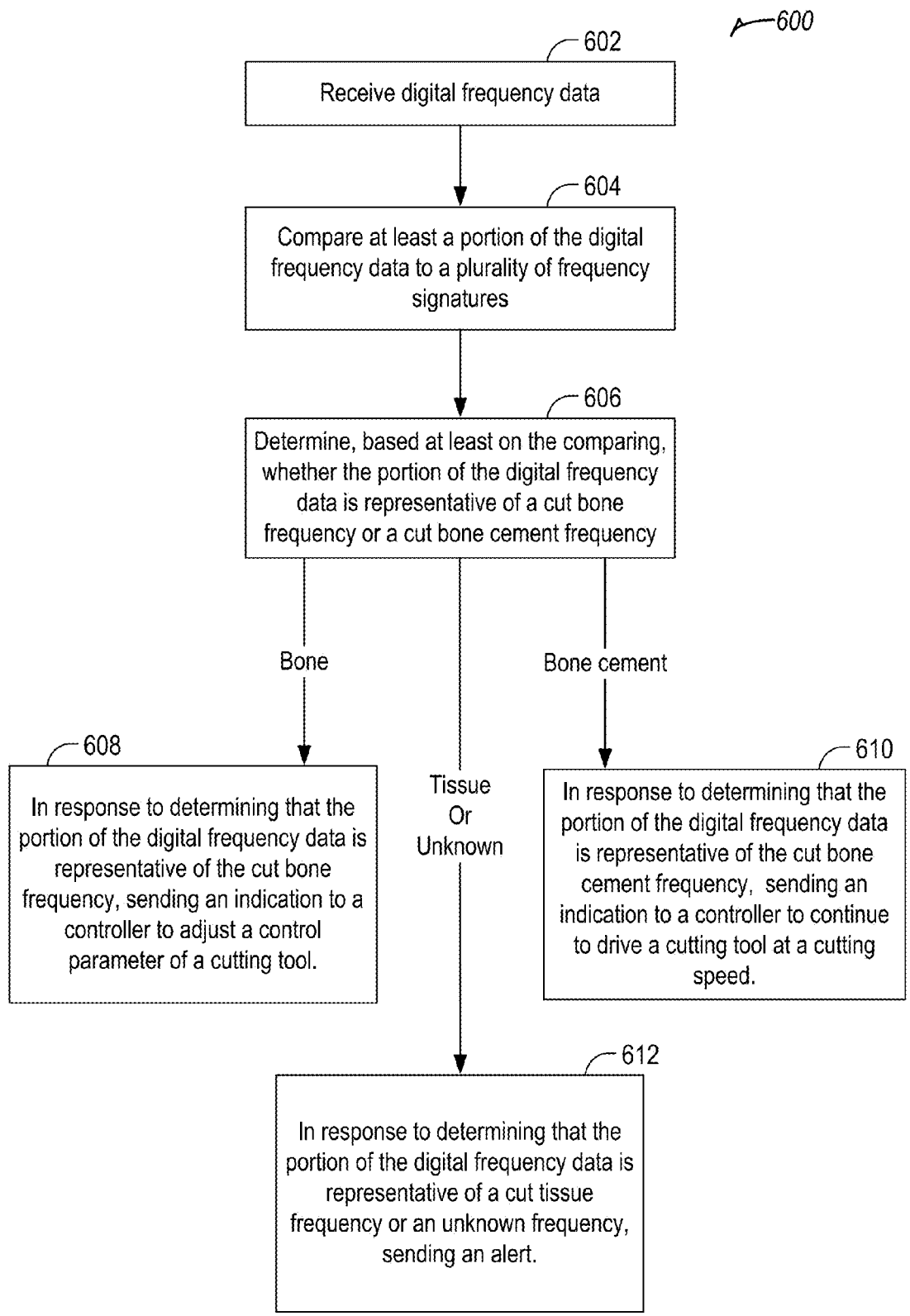
FIG. 6 is a flowchart that illustrates an example of a method for bone cement removal.

FIG. 6 is a flowchart that illustrates an example of a method 600 for bone cement removal. The method 600 includes an operation 602 to receive digital frequency data. The digital frequency data may be received from a microphone via a digital signal processor (DSP). For example, the microphone may send a received analog signal (e.g., audio) to the DSP, which may convert the analog signal to the digital frequency data.

The method 600 includes an operation 604 to compare at least a portion of the digital frequency data to a plurality of frequency signatures. Comparing at least the portion of the digital frequency data to the plurality of frequency signatures may include comparing them using audio fingerprinting, such as an audio fingerprinting algorithm, an acoustic fingerprint algorithm, or the like.

The method 600 includes an operation 606 to determine, based at least on the comparing, whether the portion of the digital frequency data is representative of a cut bone frequency or a cut bone cement frequency. Operation 606 may include using a confidence index.

The method 600 includes an operation 608 to, in response to determining that the portion of the digital frequency data is representative of the cut bone frequency, sending an indication to a controller to adjust a control parameter of a cutting tool. In an example, sending the indication to the controller to adjust the control parameter may include sending the indication to the controller to slow, stop, or withdraw the cutting tool. In another example, method 600 may include sending an alert in response to determining that the portion of the digital frequency data is representative of the cut bone frequency.

The method 600 includes an operation 610 to, in response to determining that the portion of the digital frequency data is representative of the cut bone cement frequency, sending an indication to a controller to continue to drive a cutting tool at a cutting speed.

The method 600 includes an operation 612 to, in response to determining that the portion of the digital frequency data is representative of a cut tissue frequency or an unknown or other frequency (e.g., not cut bone, cut bone cement, or tissue), sending an alert. In another example, operation 612 includes adjusting a control parameter of a cutting tool in response to determining the digital frequency data is representative of a cut tissue frequency or an unknown frequency.

As used herein, the terms "bur" and "drill" have been used interchangeably. The use of one should not be taken to exclude the other as the system of the present invention will work with either a bur, a drill, or any other cutting element.

Figure 7:
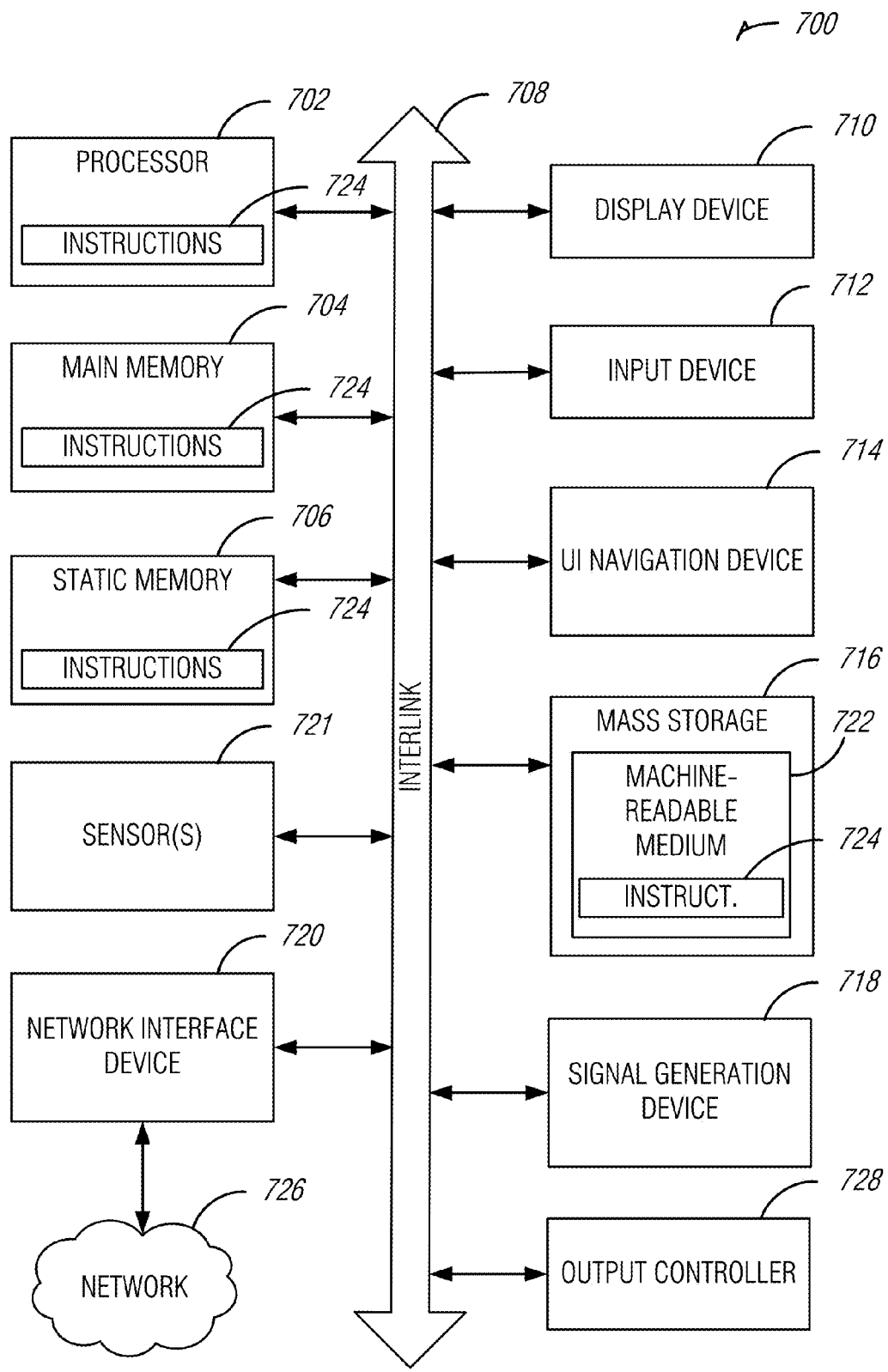
FIG. 7 is a block diagram that illustrates an example of a machine 700 within which instructions for causing the machine 700 to perform prosthesis alignment may be executed.

FIG. 7 is a block diagram that illustrates an example of a machine 700 within which instructions for causing the machine 700 to perform prosthesis alignment may be executed. In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the executions units or a loading mechanism. Accordingly, the execution units are communicatively coupled to the computer readable medium when the device is operating. In this example, the execution units may be a member of more than one module. For example, under operation, the execution units may be configured by a first set of instructions to implement a first module at one point in time and reconfigured by a second set of instructions to implement a second module.

Machine (e.g., computer system) 700 may include a hardware processor 702 (e.g., a central processing unit (GPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710, an alphanumeric input device 712 (e.g., a keyboard), and a user interface (UI) navigation device 714 (e.g., a mouse), in an example, the display unit 710, alphanumeric input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 that is non-transitory on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

VARIOUS NOTES & EXAMPLES

The foregoing discussion discloses and describes merely exemplary examples of the present invention. One skilled in the art will readily recognize from the accompanying drawings and claims that various changes or modifications may be made without departing from the spirit and scope of this invention.

Each of these non-limiting examples may stand on its own, or may be combined in various permutations or combinations with one or more of the other examples.

Example 1 includes the subject matter embodied by a system for bone cement removal, the system comprising: a controller coupled to a cutting tool, a microphone, a processor coupled to a memory device, the memory device containing instructions that, when executed by the processor, cause the system to perform operations comprising: receiving digital frequency data from the microphone, comparing at least a portion of the digital frequency data to a plurality of frequency signatures, determining, based at least in part on the comparing, whether the portion of the digital frequency data is representative of a cut bone frequency or a cut hone cement frequency, and in response to determining that the portion of the digital frequency data is representative of the cut bone frequency, sending an indication to the controller to adjust a control parameter of the cutting tool.

In Example 2, the subject matter of Example 1 may optionally include a digital signal processor, the digital signal processor coupled to a second memory device, the second memory device containing instructions that, when executed by the digital signal processor, cause the system to perform operations comprising: receiving an analog signal from the microphone, and converting the analog signal to the digital frequency data.

In Example 3, the subject matter of one or any combination of Examples 1-2 may optionally include wherein determining whether the portion of the digital frequency data is representative of a cut bone frequency or a cut bone cement frequency includes using a confidence index.

In Example 4, the subject matter of one or any combination of Examples 1-3 may optionally include wherein sending the indication to the controller to adjust the control parameter includes sending the indication to the controller to slow or stop the cutting tool.

In Example 5, the subject matter of one or any combination of Examples 1-4 may optionally include wherein the operations further comprise in response to determining that the portion of the digital frequency data is representative of a bone cement frequency, sending an indication to the controller to continue to drive the cutting tool at the cutting speed.

In Example 6, the subject matter of one or any combination of Examples 1-5 may optionally include wherein sending the indication to the controller to adjust the control parameter includes sending the indication to the controller to withdraw the cutting tool.

In Example 7, the subject matter of one or any combination of Examples 1-6 may optionally include wherein the operations further comprise in response to determining that the portion of the digital frequency data is representative of a bone frequency, sending an alert.

In Example 8, the subject matter of one or any combination of Examples 1-7 may optionally include wherein the controller includes an actuated controller, and further comprising a second microphone.

In Example 9, the subject matter of one or any combination of Examples 1-8 may optionally include wherein comparing at least the portion of the digital frequency data to the plurality of frequency signatures includes comparing using audio fingerprinting.

Example 10 includes the subject matter embodied by a machine readable medium including instructions to, when executed by an electronic device, cause the electronic device to perform operations comprising: receiving digital frequency data from a microphone, comparing at least a portion of the digital frequency data to a plurality of frequency signatures, determining, based at least in part on the comparing, whether the portion of the digital frequency data is representative of a cut bone frequency or a cut bone cement frequency, and in response to determining that the portion of the digital frequency data is representative of the cut bone frequency, sending an indication to a controller to adjust a control parameter of a cutting tool.

In Example 11, the subject matter of Example 10 may optionally include receiving an analog signal from the microphone, and converting the analog signal to the digital frequency data.

In Example 12, the subject matter of one or any combination of Examples 10-11 may optionally include wherein sending the indication to the controller to adjust the control parameter includes sending the indication to the controller to slow or stop the cutting tool.

In Example 13, the subject matter of one or any combination of Examples 10-12 may optionally include wherein sending the indication to the controller to adjust the control parameter includes sending the indication to the controller to withdraw the cutting tool.

In Example 14, the subject matter of one or any combination of Examples 10-13 may optionally include wherein comparing at least the portion of the digital frequency data to the plurality of frequency signatures includes comparing using audio fingerprinting.

Example 15 includes the subject matter embodied by a system for bone cement removal, the system comprising: a plurality of microphones, a graphic processor unit (GPU) coupled to a memory device, the memory device containing instructions that, when executed by the GPU, cause the system to perform operations comprising: receiving digital frequency data from the plurality of microphones via a digital signal processor (DSP), comparing at least a portion of the digital frequency data to a plurality of frequency signatures, determining, based at least in part on the comparing, whether the portion of the digital frequency data is representative of a cut bone frequency or a cut bone cement frequency, and in response to determining that the portion of the digital frequency data is representative of the cut bone frequency, sending an indication to a controller to adjust a control parameter of a cutting tool.

In Example 16, the subject matter of Example 15 may optionally include wherein the plurality of frequency signatures are patient independent.

In Example 17, the subject matter of one or any combination of Examples 15-16 may optionally include wherein comparing at least the portion of the digital frequency data to the plurality of frequency signatures includes comparing using audio fingerprinting.

In Example 18, the subject matter of one or any combination of Examples 15-17 may optionally include wherein receiving digital frequency data from the plurality of microphones via a digital signal processor (DSP) includes receiving digital frequency data via the DSP periodically each millisecond.

In Example 19, the subject matter of one or any combination of Examples 15-18 may optionally include wherein comparing at least the portion of the digital frequency data to the plurality of frequency signatures includes comparing at least the portion of the digital frequency data to the plurality of frequency signatures in real time each millisecond.

In Example 20, the subject matter of one or any combination of Examples 15-19 may optionally include wherein sending the indication to the controller to adjust the control parameter includes sending the indication to the controller to slow, stop, or withdraw the cutting tool.

Example 21 includes the subject matter embodied by a method for bone cement removal, the method comprising: receiving digital frequency data from a microphone, comparing, at a processor, at least a portion of the digital frequency data to a plurality of frequency signatures, determining, based at least in part on the comparing, whether the portion of the digital frequency data is representative of a cut bone frequency or a cut bone cement frequency, and in response to determining that the portion of the digital frequency data is representative of the cut bone frequency, sending an indication to a controller to adjust a control parameter of a cutting tool.

In Example 22, the subject matter of Example 21 may optionally include receiving, at a digital signal processor (DSP), an analog signal from the microphone, and converting the analog signal to the digital frequency data.

In Example 23, the subject matter of one or any combination of Examples 21-22 may optionally include wherein determining whether the portion of the digital frequency data is representative of the cut bone frequency or the cut bone cement frequency includes using a confidence index.

In Example 24, the subject matter of one or any combination of Examples 21-23 may optionally include wherein sending the indication to the controller to adjust the control parameter includes sending the indication to the controller to slow or stop the cutting tool.

In Example 25, the subject matter of one or any combination of Examples 21-24 may optionally include, in response to determining that the portion of the digital frequency data is representative of the bone cement frequency, sending an indication to the controller to continue to drive the cutting tool at the cutting speed.

In Example 26, the subject matter of one or any combination of Examples 21-25 may optionally include wherein sending the indication to the controller to adjust the control parameter includes sending the indication to the controller to withdraw the cutting tool.

In Example 27, the subject matter of one or any combination of Examples 21-26 may optionally include, in response to determining that the portion of the digital frequency data is representative of a bone frequency, sending an alert.

In Example 28, the subject matter of one or any combination of Examples 21-27 may optionally include wherein the controller includes an actuated controller, and further comprising a second microphone.

In Example 29, the subject matter of one or any combination of Examples 21-28 may optionally include wherein comparing at least the portion of the digital frequency data to the plurality of frequency signatures includes comparing using audio fingerprinting.

Example 30 includes at least one machine-readable medium including instructions for receiving information, which when executed by a machine, cause the machine to perform any of the methods of Examples 21-29.

Example 31 includes an apparatus comprising means for performing any of the methods of Examples 21-29.

Example 32 includes the subject matter embodied by a system for controlling a cutting element during a cement removal process during a surgical revision comprising: one or a plurality of microphones, an electronic interface, a computer, a database, a controller, and a cutting element; wherein the one or a plurality of microphones record sound made during the cement removal process and deliver it to the electronic interface, the electronic interface transforms the sound to a frequency domain representation and delivers that representation to the computer, the computer compares the frequency representation to previously recorded signatures that are stored in the database and then generates signals that are sent to the controller for controlling the cutting element when appropriate.

In Example 33, the subject matter of Example 31 may optionally include wherein the signals direct the controller to stop or slow the cutting element when an appropriate frequency is detected.

In Example 34, the subject matter of one or any combination of Examples 32-33 may optionally include wherein the signals direct the controller to retract the cutting element when an appropriate frequency is detected.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A system for bone cement removal, the system comprising:
   a controller coupled to a cutting tool;
   a microphone;
   a processor coupled to a memory device, the memory device containing instructions that, when executed by the processor, cause the system to perform operations comprising:
   receiving digital frequency data from the microphone,
   comparing at least a portion of the digital frequency data to a plurality of frequency signatures using audio fingerprinting, determining, based at least in part on the comparing, whether the portion of the digital frequency data is representative of a cut bone frequency or a cut bone cement frequency, and in response to determining that the portion of the digital frequency data is representative of the cut bone frequency, sending an indication to the controller to adjust a control parameter of the cutting tool.

2. The system of claim 1, further comprising a digital signal processor, the digital signal processor coupled to a second memory device, the second memory device containing instructions that, when executed by the digital signal processor, cause the system to perform operations comprising:

receiving an analog signal from the microphone; and
converting the analog signal to the digital frequency data.

3. The system of claim 1, wherein determining whether the portion of the digital frequency data is representative of the cut bone frequency or the cut bone cement frequency includes using a confidence index.

4. The system of claim 1, wherein sending the indication to the controller to adjust the control parameter includes sending the indication to the controller to slow or stop the cutting tool.

5. The system of claim 1, wherein the operations further comprise in response to determining that the portion of the digital frequency data is representative of the cut bone cement frequency, sending an indication to the controller to continue to drive the cutting tool at the cutting speed.

6. The system of claim 1, wherein sending the indication to the controller to adjust the control parameter includes sending the indication to the controller to withdraw the cutting tool.

7. The system of claim 1, wherein the operations further comprise in response to determining that the portion of the digital frequency data is representative of the cut bone frequency, sending an alert.

8. The system of claim 1, wherein the controller includes an actuated controller, and further comprising a second microphone.

9. A system for bone cement removal, the system comprising:

a plurality of microphones;
a graphic processor unit (GPU) coupled to a memory device, the memory device containing instructions that, when executed by the GPU, cause the system to perform operations comprising:

receiving digital frequency data from the plurality of microphones via a digital signal processor (DSP), comparing at least a portion of the digital frequency data to a plurality of frequency signatures using audio fingerprinting, determining, based at least in part on the comparing, whether the portion of the digital frequency data is representative of a cut bone frequency or a cut bone cement frequency, and in response to determining that the portion of the digital frequency data is representative of the cut bone frequency, sending an indication to a controller to adjust a control parameter of a cutting tool.

10. The system of claim 9, wherein the plurality of frequency signatures are patient independent.

11. The system of claim 9, wherein receiving digital frequency data from the plurality of microphones via a digital signal processor (DSP) includes receiving digital frequency data via the DSP periodically each millisecond.

12. The system of claim 9, comparing at least the portion of the digital frequency data to the plurality of frequency signatures includes comparing at least the portion of the digital frequency data to the plurality of frequency signatures in real time each millisecond.

13. The system of claim 9, wherein sending the indication to the controller to adjust the control parameter includes sending the indication to the controller to slow, stop, or withdraw the cutting tool.

* * * * *